United States Patent [19]

Ohama et al.

[11] Patent Number: 5,246,663
[45] Date of Patent: Sep. 21, 1993

[54] ISOTHIOCYANATE VAPOR-GENERATING AGENT, GERM-DESTROYING TREATMENT METHOD USING ISOTHIOCYANATE VAPORS AND APPARATUS THEREFOR

[76] Inventors: Chiaki Ohama, 1-25-1, Chiyozakicho, Naka-ku, Yokohama-shi, Kanagawa-ken; Keisuke Kato, 1-3-1-901, Minamiyama, Shiroi-machi, Inba-gun, Chiba-ken, both of Japan

[21] Appl. No.: 826,872

[22] Filed: Jan. 28, 1992

Related U.S. Application Data

[62] Division of Ser. No. 613,710, Jan. 31, 1991, abandoned.

[51] Int. Cl.[5] .......................... A61L 9/00; A61L 2/00; B65D 25/00
[52] U.S. Cl. ...................................... 422/30; 422/292; 422/31; 220/87.1
[58] Field of Search .......................... 422/292, 30, 31; 220/87.1

[56] References Cited

U.S. PATENT DOCUMENTS 3,975,204  8/1976  Zdarsky et al. ................... 127/42
4,344,250  8/1982  Fahlstrom ........................ 47/57.5

OTHER PUBLICATIONS

Hackh's Chemical Dictionary, 4th Edition, pp. 441 and 442.

*Primary Examiner*—James C. Housel
*Assistant Examiner*—N. Bhat
*Attorney, Agent, or Firm*—Lorusso & Loud

[57] ABSTRACT

An isothiocyanate vapor-generating agent containing a solution of an isothiocyanate dissolved in an oily liquid having a vapor pressure of 2 mmHg or less at 30° C. A germ-desroying treatment method using vapors of an isothiocyanate and a germ-destroying treatment apparatus are also disclosed.

2 Claims, 3 Drawing Sheets

ISOTHIOCYANATE VAPOR-GENERATING AGENT, GERM-DESTROYING TREATMENT METHOD USING ISOTHIOCYANATE VAPORS AND APPARATUS THEREFOR

This is a division, of application Ser. No. 07/613,710 filed Jan. 31, 1991, now abandoned.

TECHNICAL FIELD

This invention relates to an isothiocyanate vapor-generating agent, a germ-destroying treatment method using isothiocyanate vapors and an apparatus for carrying out a germ-destroying treatment using an isothiocyanate.

TECHNICAL BACKGROUND

Various foods, glass products such as lenses, leather products such as leather boots, leather jumpers and fur coats and products of paints and pastes formed of starch or cellulose are apt to mold. This considerably reduces validity of the goods or calls for waste disposal thereof.

Apart from mold, increased growth of harmful microorganisms, too, considerably reduces validity of the goods or demands for waste disposal thereof. For example, in the case of foods, there are caused problems of fermentation and food poisoning due to increased growth of bacteria.

It is known to seal-pack an article together with an oxygen absorber with a packing material and to maintain the oxygen concentration within the pack below 1% or less for the purpose of preventing the article from molding. While this method can effectively prevent generation of mold by aerobic bacteria, this cannot be an effective means for preventing increase and growth of anaerobic bacteria which account for food poisoning or fermentation.

It is also known to seal-pack an article together with an ethanol-emanating agent and to fill the inside of the pack with ethanol vapors for the purpose of preventing the formation of mold and the growth of ordinary bacteria. With this method, satisfactory effect cannot be obtained unless ethanol which is expensive is used in a relatively large amount.

Further, a number of mildew-proofing agents and anti-bacterial agents are hitherto known. Most of these chemicals, however, have toxicity to human bodies so that the use thereof is subjected to severe restriction.

A number of natural products having an antimicrobial action are hitherto known. Especially, Eutrema wasabi is known to have an excellent germicidal activity. It is also known to subject food to a germ-destroying treatment using an isothiocyanate (hereinafter referred to simply as ISOTC) which is a major component of wasabi. For example, Japanese Published Unexamined Patent Application No. Sho-57-99182 discloses an aqueous emulsion composition obtained by emulsion-dispersing, in water in the presence of an emulsifier, a solution of ISOTC dissolved in an oil. This aqueous emulsion composition is used by mixing into a food so as to sterilizing the food. However, the incorporation of such an aqueous emulsion into foods is not preferable not only because taste of the foods deteriorates but also because ISOTC in foods is apt to decompose. Japanese Published Unexamined Patent Application No. Sho-58-63348 discloses a method for Preserving vegetables and fruits wherein the vegetables and fruits are packed in a packaging vessel together with a synthetic zeolite which has a pore diameter of 5–10 Å and which is impregnated with ISOTC in a proportion of about 5% by weight. The ISOTC-impregnated zeolite does not emanate an effective amount of ISOTC vapors in air. It can adsorb moisture in air when subjected to a high humidity condition of a relative humidity of 90% or more with the simultaneous generation of ISOTC adsorbed therein. This known method has problems because the synthetic zeolite with a pore diameter of 5–10 Å to be used as an absorbent of ISOTC is expensive and the amount of ISOTC adsorbed thereto is very low of about 5% by weight. The known, ISOTC-absorbed, synthetic zeolite has also a drawback because it cannot emanate ISOTC vapors unless it is subjected to a high humidity condition. Thus, the ISOTC-adsorbed, synthetic zeolite is not effectively utilized as a general ISOTC vapor-generating agent.

As described in the foregoing, several techniques for destroying germs with the use of ISOTC which is a major ingredient of wasabi are known. However, none of them are not satisfactory from the practical standpoint.

It is the prime object of the present invention to provide an easy to handle, ISOTC vapor-generating agent utilizing ISOTC which is a major ingredient of wasabi and various products containing such an agent.

Another object of the present invention is to provide a method for germ-destroying treatment of various articles using ISOTC vapors.

It is a further object of the present invention to provide an apparatus for carrying out germ-destroying treatment using ISOTC.

The present inventors have made various studies in order to accomplish the above objects and, as a result, have found, on the basis of payment of attention to the fact that ISOTC is an oily liquid, that the amount of ISOTC generated can be advantageously and finely controlled by controlling the concentration of ISOTC in a solution obtained by dissolving ISOTC in an oily liquid having a vapor pressure at 30° C. of 2 mmHg or less and that germ-destroying treatment of various articles can be effectively advantageously performed, without encountering any noticeable deterioration of working environments by contacting the various articles with ISOTC vapors generated from the solution.

The present inventors have also found that an easy to handle ISOTC-vapor generating agent capable of generating ISOTC vapors in a controlled amount is obtainable by impregnating a porous adsorbent with the above ISOTC solution.

The present inventors have further found that an easy to handle ISOTC-vapor generating agent capable of generating ISOTC vapors in a controlled amount is obtainable by incorporating the above ISOTC solution into a gel-like substance or by encapsulation thereof.

The present inventors have further found that various products with germ-destroying action is obtainable by using the above-mentioned ISOTC vapor-generating agent.

The present inventors have further found that plastic films such as polyethylene films and polypropylene films have a high gas-permeability to ISOTC vapors and that an article can be effectively treated for destroying germs when seal-packed with such a plastic film and when contacted with ISOTC vapors.

DISCLOSURE OF THE INVENTION

In accordance with the present invention there is provided a method for the treatment of an article for destroying germs characterized in that the article is contacted with vapors generated from a solution of an ISOTC dissolved in an oily liquid in a proportion of 0.01-50% by weight concentration, said oily liquid having a vapor pressure of 2 mmHg or less at 30° C. or from an ISOTC vapor-generating agent containing said solution.

In accordance with the present invention there is provided an ISOTC vapor-generating agent containing a porous substance impregnated with the above ISOTC solution.

In accordance with the present invention there is provided an ISOTC vapor-generating agent composed of an encapsulated substance containing the above ISOTC solution.

In accordance with the present invention there is provided an ISOTC vapor-generating agent composed of a gel-like substance containing the above ISOTC solution.

In accordance with the present invention there is provided various products exhibiting a germ-destroying action and containing the above ISOTC vapor-generating agent.

In accordance with the present invention there is provided a method for the germ-destroying treatment for an article characterized by contacting the article, packed with a material permeable to ISOTC vapors, with ISOTC vapors.

In accordance with the present invention there is provided a method for the treatment of an article for destroying germs characterized in that said method comprises steps of: introducing an ISOTC in the form of vapors or liquid microparticles into a germ-destroying treatment chamber to form an ISOTC vapor-containing atmosphere in said germ-destroying treatment chamber; feeding the article to said germ-destroying treatment chamber; contacting the article with a gas of the ISOTC vapor-containing atmosphere in said germ-destroying treatment chamber to effect germ-destroying treatment; discharging the atmosphere gas from said germ-destroying treatment chamber after the germ-destroying treatment; and removing the ISOTC vapors from the discharged gas.

In accordance with the present invention there is provided an apparatus for the treatment of an article for destroying germs, characterized in that said apparatus comprises a germ-destroying treatment chamber provided with a feed conduit for introducing an ISOTC into said treatment chamber therethrough and a discharge conduit for discharging the atmosphere gas from said treatment chamber therethrough; a storage vessel connected to said feed conduit and accommodating the ISOTC; and a device connected to said discharge conduit for removing vapors of the ISOTC.

The term "germ-destroying action" used in the present invention is intended to refer to "antimicrobial action" which includes both germicidal action and germistatic action. The term "germ" herein is intended to involve bacteria, fungi, spore, alga and other harmful microorganisms.

The ISOTC vapor-generating agent according to the present invention is applied, by virtue of strong germ-destroying action of ISOTC vapors generated therefrom, to a food field and various other fields which involve problems of growth of harmful microorganisms. For example, the agent is used for the prevention of mold of foods or for the prevention of mold which grows on various solid surfaces such as glasses and concrete walls. Further, the agent is used for the prevention of rot or fermentation of foods and for prevention of deterioration of the freshness thereof. Furthermore, the agent is used for destroying body odors such as armpit odors, sweat odors and foot odors or for preventing the generation of such odors through the prevention of bacterial decomposition of sweat and sebum. Because of its fungicidal effect, the agent may be used for the treatment of skin disease caused by fungi such as water-eczema or ringworm.

The term "article" used in the present specification is intended to involve various products, such as foods, in which growth of harmful microorganisms poses problems.

As the isothiocyanate (ISOTC), there may be used various aliphatic and aromatic esters of isothiocyanic acid. Preferably, allyl isothiocyanate ($CH_2{=}CHCH_2NCS$) and alkyl isothiocyanate (RNCS, R: alkyl) are used. In the present invention, mustard oil may be used as such.

The present invention will next be described in detail.

(1) Preparation of ISOTC Solution in Oily Liquid

The solution emanating ISOTC vapors according to the present invention is a solution obtained by dissolving ISOTC in an oily liquid. As the oily liquid, there is used one which has vapor pressure (saturated vapor pressure) at 30° C. of 2 mmHg or less, preferably 1 mmHg or less. Since a solution of ISOTC dissolved in an oily liquid having such a low vapor pressure can significantly suppress the vaporization of ISOTC and since vapors emanating from such a solution contains almost no vapors of the oily liquid and substantially consist of the ISOTC vapors, the contact of an article with such vapors does not cause troubles resulting from the vapors of the oily liquid. An oily liquid having a boiling point of at least 180° C., preferably at least 200° C., more preferably 230° C., is generally advantageously used. As the oily liquid, there may be mentioned, for example, fats and oils such as olive oil, sesame oil, safflower oil, soybean oil, tsubaki oil, corn oil, rape oil, castor oil, sunflower oil, cottonseed oil, peanut oil, cacao butter, palm oil, clove oil, coconut oil, beef tallow, fish oil, hardened oil, turtle oil and yolk oil; waxes such as liquid lanolin; hydrocarbon oils such as liquid paraffin, liquid polyisobutylene and squalane; higher fatty acid oils such as oleic acid, ricinolic acid and lysinol; higher alcohols such as octyl alcohol and oleil alcohol; polyalcohols such as polyethylene glycol, polypropylene glycol and glycerin; and ester oils such as linol acetate and hexyl laurate. It is preferred that the oily liquid to be used in the present invention be preferably odorless or almost odorless.

The amount of ISOTC dissolved in the oily liquid is 0.01–50% by weight, preferably 0.1–40% by weight based on the oily liquid solution of ISOTC.

ISOTC generates a strong irritating odor even if present in a small amount and is difficult to handle. However, when used in the form of an oily liquid solution as described above, vaporization of ISOTC is effectively prevented so that ISOTC can be handled without difficulty. The ISOTC solution may be used as such as an ISOTC vapor-generating agent.

In dissolving ISOTC in the oily liquid, various auxiliary components may be added or dissolved thereinto as desired. Examples of such auxiliary components include a surfactant; a high molecular weight substance; a higher alcohol, a higher fatty acid, a fatty acid ester or a fat and oil which are solids at ambient temperature; a colorant; viscosity-controlling agent; and an antioxidant. Further, a lower alcohol such as ethanol or propyl alcohol or a low boiling point solvent such as acetone, methyl ethyl ketone, ether, ethyl acetate or hexane may be added in a small amount as an auxiliary component to control the amount of ISOTC vaporized from the oily liquid.

The ISOTC-containing oily liquid according to the present invention may be prepared by dispersing ISOTC-containing seeds or cells, as such or after pulverization, into an oily liquid. The amount of the seeds or cells dispersed in the oily liquid is 1–80% by weight, preferably 10–60% by weight based on the oily liquid. Such an ISOTC-containing oily liquid may be used under a condition where the seeds or cells are present.

(2) Preparation of ISOTC Vapor-Generating Agent in Solid or Gel-Like Form, and Products Containing the ISOTC Vapor-Generating Agent The ISOTC vapor-generating agent may be obtained by impregnating a porous substance with the above-mentioned oily liquid solution of ISOTC (hereinafter referred to also merely as ISOTC solution). When the porous substance is impregnated with ISOTC by itself, a-large amount of ISOTC vapors is generated at the time of impregnation of the porous substance with ISOTC because of the high evaporation rate thereof. As a result, the working environment becomes poor due to ISOTC vapors. Additionally, it becomes difficult for the porous substance to stably support ISOTC for a long period of time since vaporizability of ISOTC carried by the porous substance is still high. According to the present invention, such difficulties have been overcome by supporting ISOTC as a solution dissolved in the above oily liquid to a porous substance by impregnation. While ISOTC easily reacts with water and is poor in storage stability, this problem has been also solved by using it in the form of a solution in the above-mentioned oily liquid.

As the porous substance, those which are generally used as an absorbent, a filler, etc. may be used. Examples of such substances include clay or clay minerals such as diatomaceous earth, yellow earth, clay, talc, zeolite, attapulgite and sepiolite and other substances such as activated carbon, silica, silica gel, alumina, magnesia, silica-alumina, silica-magnesia and synthetic aluminosilicate. As the porous substance, there may be used those of a variety of shapes such as in the form of powder, pellet, sphere, column and cylinder. As the porous substances, it is preferable to use calcined or dried materials from which moisture has been sufficiently removed.

Impregnation of the porous substance with the solution may be performed by a method wherein the porous substance is mixed with the ISOTC solution, a method wherein the ISOTC solution is sprayed over the porous substance, a method wherein the porous substance is immersed in the ISOTC solution, or the like method. The proportion of the ISOTC solution supported by impregnation to the porous substance is not greater than the saturated absorbing capacity of the porous substance and, generally, 1–100 parts by weight per 100 parts by weight of the porous substance. Preferred content is suitably determined according to the kind of the ISOTC solution and the kind of the porous substance.

In the present invention, when the porous substance impregnated with the ISOTC solution is in the form of powder, it is possible to shape it by a conventional shaping method into tablet, spheres, columns, pellets, etc. The shaping may be effected by a tablet shaping method, an extrusion molding method, etc. In performing the shaping, a molding aid is used. Examples of the molding aid include organic binders such as carboxymethyl cellulose, polyvinyl alcohol and sodium alginate and inorganic binders such as bentonite, kaolin, alumina hydrogel and silicic acid hydrogel. As the molding aid, various short fibers such as gypsum whisker may also be used. For the purpose of controlling the emanation of ISOTC, the ISOTC solution-containing porous substance may be coated with a resin pervious to ISOTC vapors. Provision of such a coating can further suppress the emanation of ISOTC from the porous substance.

Another type of the ISOTC vapor-generating agent may be obtained by encapsulating the above-mentioned ISOTC solution. The encapsulation may be performed by various known methods, for example, a method wherein the ISOTC solution and a high molecular weight solution are simultaneous)y ejected into an aqueous medium through inner and outer nozzles, respectively, of a dual liquid nozzle, a surface polymerization method, etc. The encapsulation may also be effected by a method wherein the ISOTC or a porous substance impregnated with the ISOTC solution is mixed with a melt of a fusible material which is solid at room temperature and which has a melting point of 100° C. or less, preferably in the range of 40°–60° C., the resulting mixture being cooled for solidification and then ground. In this case, as the fusible material, there may be mentioned higher alcohols or esters thereof, fats and oils, waxes, etc. The encapsulation may also be effected by a method wherein the ISOTC or a porous substance impregnated with the ISOTC solution is mixed with a melt of a thermosetting resin composition (such as epoxy resin composition or unsaturated polyether resin composition) which is liquid at room temperature or at a temperature of 100° C. or less, the resulting mixture being cooled for solidification and then ground. A reaction of the ISOTC solution with an inclusion compound-forming agent such as cyclodextrin, urea, etc. may also give encapsulated materials.

In the present invention, the above-mentioned ISOTC solution, the porous substance impregnated with the ISOTC solution, the shaped article of the ISOTC solution-containing porous substance and the encapsulated material of the ISOTC solution may be used in a state seal-packed with a packing material. As the packing material, there may be used one at least a portion of which is pervious to ISOTC vapors. Illustrative of such packing materials are films, sheets and vessels pervious to ISOTC vapors and formed of a plastic such as polypropylene, polyethylene or ethylene/vinyl acetate copolymer. A packing material formed of a plastic impervious to ISOTC vapors may be used as a packing material pervious to ISOTC vapors by forming fine holes using, for example, a laser beam. In addition, paper, non-woven fabric, a surface-treated material of paper or non-woven fabric, or a laminate of a paper, non-woven fabric or cloth with a plastic film pervious to ISOTC vapors may also be used.

A further ISOTC vapor-generating agent according to the present invention may be obtained by incorporating the above-mentioned ISOTC solution in a gel-like substance.

Various kinds of conventionally known gel-like substances may be used. Illustrative of these substances are agar, carrageenan, gelatin, carboxymethyl cellulose, starch, alginic acid, polyvinyl alcohol and dextrin. The incorporation of the ISOTC solution into the gel-like substance may be effected by a method in which the ISOTC solution is mixed and dispersed in a previously formed gel-like substance, a method in which the ISOTC solution is added during the preparation of the gel-like substance, especially to a raw material for the preparation of the gel-like substance, or the like method. The content of the ISOTC in the gel-like substance is generally 0.05–20% by weight, preferably 0.5–10% by weight. A concrete content of ISOTC is adequately determined according to the object of use of the gel like substance. In case where the ISOTC solution is incorporated into the gel-like substance, the ISOTC solution may be used as a previously encapsulated form.

The above-mentioned ISOTC vapor-generating agent according to the present invention is generally used after being filled or packed in a bag of a paper which has been subjected to a water-repelling or oil-repelling treatment or in a bag or vessel formed of a plastic. As a bag of a plastic film or vessel, there is used one which is pervious to ISOTC vapors.

According to the present invention, various articles showing germicidal activity may be obtained by using the above-mentioned ISOTC vapor-generating agent. As one such article, for example, there is provided a conventionally known coating composition such as an adhesive composition, a paint composition or ink composition having incorporated thereinto, as a blending ingredient, the above-mentioned ISOTC solution, powdery porous substance impregnated with the ISOTC solution or encapsulated material of the ISOTC solution. These compositions may be in the form of a liquid or a film. These articles may be utilized in a variety of fields such as foods, packing materials, construction materials, etc. as a coating composition having germicidal activity.

According to the present invention, there is also provided a sheet-like material having a sheet or film, such as paper, non-woven fabric or a plastic film, having coated thereon a coating composition containing the above-mentioned ISOTC. In this case, the coating may be formed on one or both sides of the sheet-like material or between respective plural laminated sheets. The sheet-like material may be used, as a sheet-like material having a germicidal activity, in various fields such as: of foods, packing materials, construction materials, etc.

According to the present invention, boards (hardboard, semihard-board, insulation board, particle board, etc.) having germicidal activity may be obtained by mixing the above-mentioned powdery porous substance impregnated with the ISOTC solution with cellulosic materials such as wood powder, wood chips, etc. together with an adhesive, followed by molding into plates. Also, a gypsum board having germicidal activity may be obtained by mixing the above ISOTC-containing powdery porous substance with calcined gypsum together with powder such as pulp powder or wood powder, followed by molding into plates. A plastic board having germicidal activity may be further obtained by mixing the powdery porous substance impregnated with the ISOTC solution with a resin composition hardenable at ambient or a low temperature, such as an epoxy resin composition or an unsaturated polyester resin composition, followed by molding and hardening. The articles may be used in the field of construction materials as a germicidal or mildew-proof board (plate-like material).

Furthermore, according to the present invention, a spray solution containing ISOTC or ISOTC solution dissolved in ethanol in a proportion of 0.01–5% by weight concentration. In this case, the ethanol may be water-containing ethanol having a water content of 50% by weight or less. Since ethanol has by itself strong germicidal activity and mildew-proofing property, the use thereof is very Preferable. When ISOTC in the form of a solution of a hardly vaporizable liquid is dispersed into ethanol and the dispersion, as a spray solution, is sprayed on an object, it is possible to control the amount of ISOTC evaporated from the deposit solution depositing thereonto. When ISOTC in the form of a solution of an oily liquid is dissolved in ethanol, a spray solution having good storage stability may be obtained even when the ethanol is a water-containing alcohol. To the spray solution according to the present invention may be added auxiliary components such as a surfactant, a high molecular weight substance, viscosity controlling agent, antioxidant and finely divided absorbent particles.

The spray solution of this invention is charged to a suitable spray device and is used by spraying liquid particles through its nozzle. A suitable spray device preferably used in the present invention is of an aerosol-type using an injection agent. Namely, an aerosol type spray device using the spray solution of this invention may be obtained by placing the spray solution in an airtight vessel equipped with an injection nozzle and, then charging under pressure an injection agent thereto. As the injection agent, there may be used conventionally known agent, for example, a liquefied hydrocarbon gas such as propane, n-butane, isobutane, n-pentane, isopentane or a mixture thereof. Generally, a liquefied petroleum gas or a liquefied natural gas is suitably used. A flon gas such as fluorodichloromethane may be also be used.

Since a solution of ISOTC dissolved in an oily liquid having a vapor pressure of 2 mmHg or less at 30° C. shows an extremely suppressed emanation of ISOTC, handling of the solution is very easy. Additionally, since the ISOTC solution gradually emanates ISOTC for a long period of time, retentivity in ISOTC vapor-generating effect of the solution is excellent. Therefore, the solution may be used by itself as an ISOTC vapor-generating agent and, moreover, utilized in various fields as a germicide, a mildew-proof agent, a freshness-keeping agent, a deodorizer, etc. by virtue of the germicidal property of ISOTC vapors emanated therefrom. Furthermore, the solution may be utilized in a variety of fields as a functional material having germicidal activity.

In the above-mentioned porous substance impregnated with the ISOTC solution and the above-mentioned encapsulated material of the ISOTC solution, the emanation of ISOTC vapors is much more suppressed so that they may be used, as a solid agent emanating ISOTC, in various fields such as foods, packing materials and construction materials.

The above-mentioned coating composition containing the ISOTC solution, the ISOTC solution-impregnated porous substance or the ISOTC solution-encapsulated material may be used as a functional composition having germicidal activity in various fields. A coating of the composition gradually emanates ISOTC vapors to attain desired germicidal effect.

The above-mentioned sheet-like material using the coating composition gradually emanates ISOTC vapors so that it may be utilized in various fields such as foods, packing materials, printing materials, construction materials, as a functional sheet-like material having germicidal property, mildew-proof property, freshness-keeping property and deodorizing property.

The gel-like substance according to the present invention containing the ISOTC solution emanates ISOTC vapors, in an extremely suppressed manner, gradually for a long period of time and is excellent in retentivity of germicidal activity. Thus, it is advantageously utilized in the field of foods, etc.

The spray solution according to the present invention containing the ISOTC solution is used by spraying it over an object as liquid particles. In this case, since ISOTC is sprayed in a low concentration solution state, strong irritating odor of ISOTC is so suppressed that the ambient environment is not specifically badly influenced. Since ISOTC is contacted with an object in the form of a liquid, its effect is much quicker in comparison with a case where ISOTC is contacted in the form of vapors. The spray solution is utilized in a wide variety of fields where growth of harmful microorganisms creates problems or where bad odors create problems, such as in the field of foods by virtue of its germicidal property, mildewproof property and deodorizing property. Since ISOTC exhibits antibacterial activity against favus, the spray solution of the present invention may be used for the purpose of treating skin disease (for example, treating eczema).

(3) Germ Destroying Treatment Method and Apparatus Therefor

The method for the germ-destroying treatment of an article according to the present invention includes a step of contacting the article with ISOTC vapors. The concentration of the ISOTC vapors in a gas to be contacted with the article is at least 5 ppm (v/v) but is lower than the saturation concentration in the gas. More particularly, the concentration is generally 20–5,000 ppm, preferably 50–1,000 ppm and may be suitably determined according to the article. The contact time depends upon the concentration of ISOTC in the gas and is 0.1–60 minutes, preferably 0.5–30 minutes when the concentration of ISOTC vapors is 20 ppm or more. The treatment time may be adequately determined according to the article to be treated.

In the present invention, the article to be contacted with ISOTC vapors may be packed with a plastic packing material such as of Polyethylene, polypropylene or ethylene/vinyl acetate copolymer. Investigation by the present inventors has revealed that the above-described plastic materials show high permeability to ISOTC vapors and that such an article packed with the packing material and once subjected to germ-destroying treatment is no longer susceptible to secondary contamination with harmful germs and is effectively protected from infection of harmful germs as long as the package is kept as is.

The concentration of ISOTC vapors in the gas with which the packed article is contacted is preferably higher than that used in treating an unpacked article and is generally 100–5,000 ppm.

The packing material for packing an article should be broadly construed and comprises vessels of various shapes as well as films and sheet-like materials. Suitable methods for packing an article include a method in which the article is accommodated in a bag and packed therewith;,a method in which the article is placed in an open vessel such as a tray, the open end being subsequently sealed with a film; a method in which the article is placed in an open vessel such as a tray, the vessel being subsequently entirely wrapped with a film; a method in which the article is packed in a box, the box being subsequently wrapped with a film; and a method in which the article being a liquid is placed in a plastic vessel, the vessel being subsequently closed with a lid.

The term "packing of an article" used for the purpose of the present invention is intended to include a state of packing where the article may be prevented from contamination with harmful germs and is not intended to refer only to a perfectly sealed state in which the article in the package is perfectly isolated from ambient air.

At least a portion of the packing material to be used for packing an article is pervious to ISOTC vapors. Such packing materials may be, for example, films, sheets and vessels formed of a plastic pervious to ISOTC vapors such as polypropylene, polyethylene, an ethylene/vinyl acetate copolymer or an ethylene/propylene copolymer. A packing material formed of a plastic impervious to ISOTC vapors (such as aluminum foil or nylon) may be used as a packing material pervious to ISOTC vapors by forming fine holes using, for example, a laser beam. In addition, paper, non-woven fabric, a surface-treated material of paper or non-woven fabric, or a laminate of a paper, non-woven fabric or cloth with a plastic film pervious to ISOTC vapors may also be used.

In performing the germ-destroying treatment according to the present invention, a packed or unpacked article is contacted with a gas containing ISOTC vapors. Methods for achieving this contact include, for example, a method in which the package is placed in an air-tight chamber to which ISOTC is fed in the form of vapors or sprayed in the form of liquid and a method in which the package is placed into an air-tight chamber precharged with ISOTC vapors, the package being taken out of the chamber after a predetermined period of time. One simple method included the steps of enclosing the article in a big plastic bag, and either spraying ISOTC in the form of a liquid into the bag or adding an ISOTC vapor-generating agent into the bag.

The generation of ISOTC vapors may be effected with the use of the above-mentioned ISOTC solution or various solid materials containing the ISOTC solution as well as ISOTC itself. With such ISOTC solution or solid materials containing same, ISOTC vapors slowly emanate in a controlled amount.

When a packed article is contacted with ISOTC vapors in a manner as described above, ISOTC vapors enter the package. The intruded ISOTC vapors after completion of the germ-destroying treatment permeate through the packing material and are gradually dispersed out of the package. From the standpoint of germicidal effect, it is preferred that the concentration of ISOTC vapors in the package be high and ISOTC vapors remain therein for a long period of time. In general, it is preferred that ISOTC vapors be present in a concentration of 10 ppm or more for 10 minutes or more. The concentration of ISOTC vapors in the package gradually decreases with time as the vapors are dispersed out of the package. The decrease of the concentration of ISOTC vapors may be controlled by previously incorporating an adsorbent into the package. Namely, when an absorbent is previously placed in the package, the adsorbent can adsorb ISOTC vapors during the treatment of the packed article by contact with ISOTC vapors. Thus, after the completion of the treatment, the adsorbent can still emanate ISOTC vapors so that the concentration of ISOTC vapors in the package and the retention time of the vapors may be controlled. Presence of ISOTC vapors for a long time in the package is not desirable because of the occurrence of problems that the vapors excessively migrate to the article to cause deterioration of the properties of the article. It is generally preferable to suitably select the kind of the packing material and the amount of the adsorbent so that the concentration of ISOTC vapors be decreased to 10 ppm or less within 48 hours.

An article which is not packed may be first subjected to a germ-destroying treatment and thereafter packed with a packing material to protect the article from secondary contamination with harmful germs. When there is a fear that ISOTC vapors migrate excessively to the article after the treatment to cause deterioration of the property of the article, it is desirable to previously pack the article together with an absorbent so as to let the excess ISOTC vapors absorbed by the absorbent. As such an absorbent, there may be used various porous substances mentioned previously.

The ISOTC vapors in the package of the article which has been subjected to the germ-destroying treatment are gradually dispersed out thereof with time and are almost exhausted during the circulation and sealing of the package. Therefore, a person who opens the package will not sense the irritating odor of ISOTC.

In accordance with the present invention, harmful germs which are present in a closed space can be destroyed by incorporating a gas containing ISOTC vapors into the closed space, so that the closed space and articles contained in the closed space may be sterilized. The term "closed space" used herein is intended to refer to a space whose ambient gas (air) contained therein cannot be freely communicated with the outside thereof. Such a space may be, for example, a space of various buildings such as factories and warehouses, rooms of hospitals, hatches of cargo-boats, a space defined by hoods or sheets and various containers.

In accordance with a preferred germ-destroying method of the present invention, there is provided a method for the treatment of an article for destroying germs characterized in that said method comprises steps of: introducing an ISOTC in the form of vapors or liquid microparticles into a germ-destroying treatment chamber to form an ISOTC vapor-containing atmosphere in said germ-destroying treatment chamber; feeding the article to said germ-destroying treatment chamber; contacting the article with a gas of the ISOTC vapor-containing atmosphere in said germ-destroying treatment chamber to effect germ-destroying treatment; discharging the atmosphere gas from said germ-destroying treatment chamber after the germ-destroying treatment; and removing the ISOTC vapors from the discharged gas.

According to the present invention, there is also provided an apparatus for the treatment of an article for destroying germs, characterized in that said apparatus comprises a germ-destroying treatment chamber provided with a feed conduit for introducing an ISOTC into said treatment chamber therethrough and a discharge conduit for discharging the atmosphere gas from said treatment chamber therethrough; a storage vessel connected to said feed conduit and accommodating the ISOTC; and a device connected to said discharge conduit for removing vapors of the ISOTC.

The germ-destroying method and apparatus will be explained in detail below.

In the above method and apparatus, a germ-destroying treatment chamber (also referred simply as treatment chamber in the present specification) is used. As the germ-destroying treatment chamber, there may be used one which has an inside space adapted to receive a desired article therein and which is air-tight so that the inside gas is prevented from escaping therefrom. The treatment chamber is provided with an inlet conduit for introducing ISOTC in the form of vapors or liquid microdroplets into the chamber therethrough and with an outlet pipe for discharging an ambient gas in the chamber therethrough out of the chamber.

The structure of the treatment chamber is suitably determined according to the manner in which the article is treated, i.e. whether the treatment is performed in a continuous mode or a batchwise mode. In the case of a continuous mode, the treatment chamber is provided with inlet and exit ports and with a conveyor running in circulation between these ports. In this case, the inlet and exit ports are constructed into an air-tight structure so as to prevent the ambient gas within the chamber from discharging out of the chamber. Thus, these ports are constructed so that they open only when the article enters or exits the chamber. Such entrance and exit of the air-tight structure may be constructed in conventionally known means. For example, the inlet and outlet portions of the treatment chamber may be closed with a curtain formed of a synthetic rubber or a plastic sheet to provide an air tight structure. When the germ-destroying treatment for an article is performed in a batch mode, an air tight door permitting the feeding and discharging of an article is provided in the treatment chamber.

To the ISOTC feeding conduit of the treatment chamber is connected a reservoir for containing ISOTC in the form of vapor, liquid or solid-impregnated, optionally via mixer or heater, so that ISOTC required for germ-destroying treatment is fed therefrom in the form of fine droplets or vapor.

The method for the germ-destroying treatment of an article includes the steps of (A) feeding the article to the germ-destroying treatment chamber and (B) introducing ISOTC in the form of vapor or fine droplets into the chamber to form an ISOTC vapor-containing atmosphere therein. When the germ-destroying treatment is performed in a continuous system, the step (A) for the introduction of ISOTC into the treatment chamber is followed by the step (B) for the introduction of the article thereinto. When the treatment is performed in a batch system, the step (A) for the introduction of ISOTC is preceded by the step (B) for feeding the article to the treatment chamber.

ISOTC is introduced into the treatment chamber from the reservoir through the inlet conduit in the form of vapors or fine droplets. In the case of introduction as vapors, ISOTC is previously vaporized to form an ISOTC-containing gas. When introduced as fine droplets, ISOTC is sprayed into the treatment chamber together with a gas from a mixing nozzle. As the gas, air, nitrogen gas or carbon dioxide gas may be used.

As a method for vaporizing ISOTC to form an ISOTC vapor-containing gas, there may be mentioned a method in which liquid ISOTC or a solution of ISOTC is heated to form vapors to with which a gas is subsequently mixed, a method in which ISOTC vapors are formed from an ISOTC vapor-generating agent, with which a gas is subsequently mixed, or a method in which a gas is passed through a liquid containing ISOTC so as to cause the gas to entrain ISOTC vapors. The concentration of ISOTC in the gas is 5 ppm or more. The upper limit is the amount corresponding to the saturated vapor pressure of ISOTC in the gas. Generally, the concentration is 10–5,000 ppm. When suction-mixing ISOTC or its solution with a gas using an ejector, there is obtained a gas containing both ISOTC vapors and ISOTC fine droplets. The introduction of such a gas into the treatment chamber is also an effective method.

The method of treating an article for destroying germs also includes a step (C) of contacting the article with an atmosphere gas containing ISOTC vapors. In this case, the treatment temperature varies with the kind of the article but is generally 0°–100° C., ordinarily 20°–60° C. In the case of fresh foods, ambient temperature or a low temperature of 0°–15° C. is used. The treatment pressure is not specifically limited. A reduced pressure to an increased pressure may be used. Preferably, a reduced pressure or normal pressure is used. When the germ-destroying treatment is carried out in a continuous system, it is preferable to use a reduced pressure of −5 to −50 mm in terms of water column for the purpose of preventing escape of the atmosphere gas out of the chamber at the time of opening and closing of the entrance and exit thereof. It is also preferred that the atmosphere gas within the chamber be homogeneously stirred by rotation of a fan or by withdrawing the gas from a portion of the chamber while introducing the withdrawn gas into the chamber from another portion thereof.

The germ-destroying treatment method further includes the steps of (D) discharging the atmosphere gas within the treatment chamber after completion of the germ-destroying treatment of the article and (E) removing the ISOTC gas contained in the discharged gas. The withdrawal of the atmosphere gas from the treatment chamber may be effected using a suction pump, while the removal of the ISOTC vapors from the discharged gas may be effected using a cooler, an adsorbing tower or the like device. The cooler may be of any structure as long as it can cool the gas to a temperature below that of the treatment chamber, preferably to a temperature near 0° C. As the adsorbing tower there may be used one which is filled with a gas adsorbent such as activated carbon, sepiolite, silica or alumina. The use of a combination of the cooler and the adsorbing tower is effective to perfectly remove the ISOTC vapors from the gas.

BEST MODE FOR CARRYING OUT THE INVENTION

Figure 1:
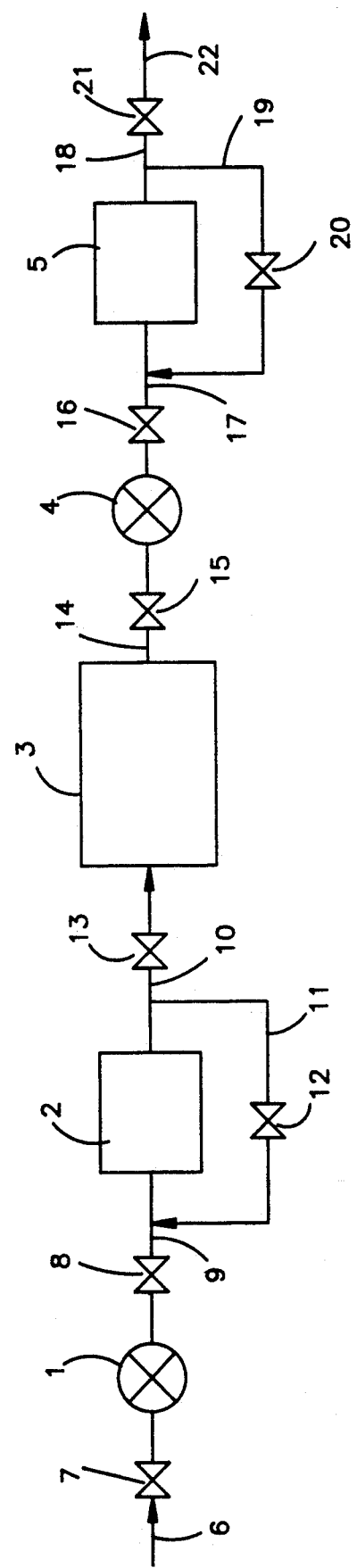
FIG. 1 is a view explanatory of performing germ-destroying treatment of an article.

Referring to FIG. 1, designated as 1 and 4 are blowers, as 2 is an ISOTC vapor generating chamber, as 3 a germ treatment chamber and as 5 an ISOTC vapor-adsorbing device. The ISOTC vapor-generating chamber 2 has a structure adapted for storing ISOTC therein. In this case, ISOTC may be in the form of a solution or a gel. Also, ISOTC may be supported by a porous substance by impregnation. The form of ISOTC is thus not specifically limited as long as ISOTC vapors can be generated.

The ISOTC vapor-adsorbing device 5 contains an adsorbent and can remove by adsorption ISOTC vapors contained in a gas fed thereto. As the adsorbent, activated carbon, sepiolite, diatomaceous earth, alumina, silica, silica gel, silica-alumina, magnesia or zeolite may be generally used, though any adsorbent may be used as long as it can adsorb ISOTC vapors.

The germ-destroying treatment of the article is carried out by operating the blower 1 to cause a gas to pass via line 6 through the vapor generating chamber 2 and to cause an ISOTC-containing gas to be discharged therefrom through line 10 and fed to the treatment chamber 3 in which the article is accommodated. As the carrier gas for ISOTC, air is generally used. Nitrogen gas or carbon dioxide gas may also be used. A portion of the gas discharged from the ISOTC vapor-generating chamber 2 may be recirculated through a line 11 and a valve 12 to a line 9 to control the concentration of ISOTC vapors in the gas passing through the line 10.

When ISOTC vapors are mixed into a gas within the treatment chamber 3 in a predetermined concentration, the blower 1 is stopped and a valve 13 is closed so that the treatment chamber is maintained in a closed state. This state is maintained for a predetermined period of time to effect the treatment of the article by absorption of ISOTC. It is preferred that a fan be provided in the treatment chamber 3 to stir the atmosphere therein for the purpose of expediting diffusion of ISOTC vapors therein. The concentration of ISOTC vapors in the treatment chamber is 5–5,000 ppm (v/v), preferably 10–2,000 ppm (v/v), on volume basis. The treatment is performed for a period of time sufficient to obtain sufficient germicidal effect on the article. The treatment time varies with the kind of the article and the concentration of ISOTC in the treatment chamber and is not determined in the same rule. Generally, however, a short period of time of 1–60 minutes, preferably 5–20 minutes is sufficient.

After completion of the germ-destroying treatment, a valve 15 is opened and the blower 4 is actuated to discharge the gas within the treatment chamber via adsorption device 5 through a line 22 to the air. In this case, for the purpose of preventing the inside of the treatment chamber from being rendered in a reduced pressure condition, a valve opening to the air is suitably connected to the treatment chamber. In the adsorbing device 5, ISOTC vapors contained in the gas are removed by adsorption due to the action of the adsorbent contained therein. The contact of the gas in the adsorbing device may be carried out for a period of time sufficient to achieve the removal by adsorption. The contact time can be controlled by recirculating a portion of the gas discharged from the adsorbing chamber 5 through a line 18 to a line 17 via line 19 and valve 20. The treatment chamber 3 and the adsorbing device 5 may be provided with heating and cooling mechanisms to effect temperature control. When the adsorbent in the adsorbing device becomes saturated, a heating medium such as steam may be passed therethrough for regeneration.

In the present invention, the mixing of ISOTC into the gas in the treatment chamber may be carried out by directly spraying ISOTC liquid or solution into the chamber in stead of feeding ISOTC vaporized in the above vapor generating chamber. The removal and separation of ISOTC from the gas may be effected using a chemical reaction with a substance reactive with ISOTC, such as a solid amine, in place of using the adsorbent.

Any chamber of an air-tight structure may be used as the germ-destroying treatment chamber 3. The gas containing ISOTC vapors may be fed to the treatment chamber 3 not only intermittently as described above but also continuously while discharging same through a line 14. In this case, part of the gas discharged from the line 14 may be recirculated to the treatment chamber through a flow control valve.

The germ-destroying treatment in the chamber 3 may be carried out in a continuous system or in a batch system. In the case of continuous system, the article is passed through the treatment chamber 3 at a constant speed.

Figure 2:
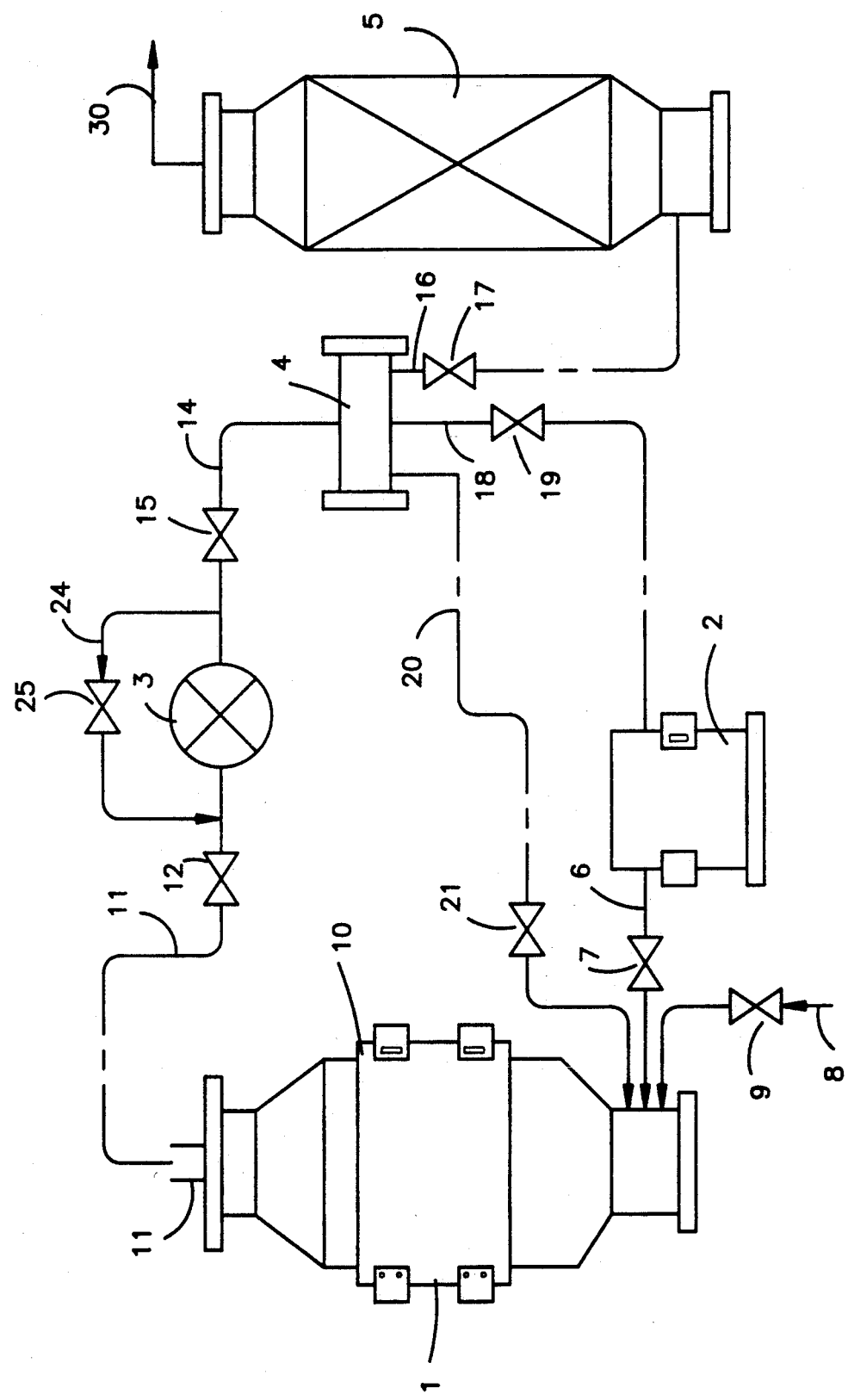
FIG. 2 is a flow diagram of an apparatus for carrying out the germ-destroying treatment of an article.
Figure 3:
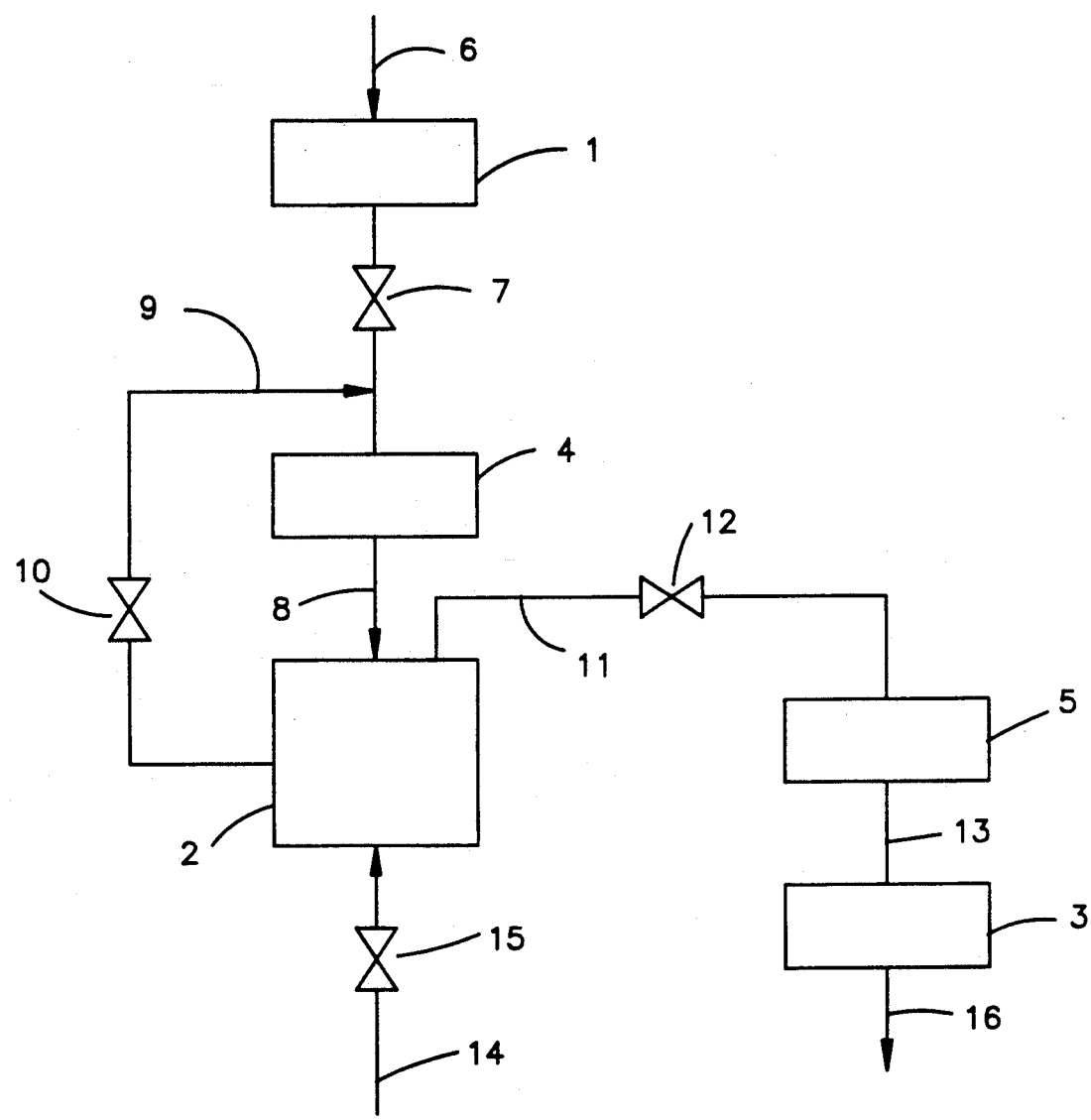
FIG. 3 is a view explanatory of performing germ-destroying treatment of a closed space.

In FIG. 2, designated as 1 is a germ-destroying treatment chamber, as 2 an ISOTC vapor-generating chamber, as 3 a blower, as 4 a gas distributor and as 5 an ISOTC adsorbing device.

The germ-destroying treatment chamber 1 and the ISOTC vapor-generating chamber 2 are interconnected by a pipe 6 provided with an open-close valve, the germ-destroying treatment chamber 1 and the blower 3 are interconnected by a pipe 11 provided with an open-close valve 12, and the blower 3 and the gas distributor 4 are interconnected by a pipe 14 provided with an open-close valve 15.

The gas distributor may be, for example, of a structure (header pipe) having a close-ended, large diameter pipe to which a gas inlet conduit and gas outlet conduits are connected.

The gas distributor 4 and the ISOTC adsorbing device 5 are interconnected by a pipe 16 having an open-close valve 17. The gas distributor 4 and the ISOTC vapor-generating chamber 2 are interconnected by a pipe 18 having an open-close valve 19. The gas distributor 4 and the germ-destroying treatment chamber 1 are interconnected by a pipe 20 having an open-close valve 21. Further, the upstream and downstream sides of the blower are interconnected by a pipe 24 having a gas flow rate controlling valve 25 so that the gas feed rate by the blower 3 may be controlled.

The open-close valves are electrically actuated and operated in a control panel.

The above-described apparatus performs germ-destroying treatments of an article as follows. First, a door 10 of the treatment chamber 1 is opened to place an article to be treated therein. After closing the door 10, the blower 3 is actuated while maintaining the valves 9, 17 and 21 in a closed state and the valves 7, 12, 15 and 19 in an open state. By the operation of the blower 3, the ambient gas (air) within the treatment chamber 1 is caused to flow and circulate successively through a recirculating path including the blower 3, gas distributor 4, the ISOTC vapor-generating chamber 2 and the treatment chamber 1. As a result of the gas recirculation, ISOTC vapors vaporized in the ISOTC vapor-generating chamber 2 are entrained in the recirculating gas and fed to the treatment chamber 1, so that the concentration of ISOTC in the treatment chamber 1 is increased with time. When the concentration of ISOTC vapors reaches a predetermined value, the valve 21 is opened and the valves 7 and 19 are closed so that the gas containing the predetermined concentration of ISOTC vapors is recirculated without preventing the passage through the ISOTC vapor-generating chamber. The detection of the concentration of ISOTC in the gas may be made with a concentration analyzer provided in the treatment chamber 1 or the pipe 11. As the concentration analyzer, any known type may be adopted such as of a gas chromatography type or an electrical conductivity meter type.

After lapse of a predetermined period of time, the valve 17 is opened while the valves 19 and 21 are closed. The operation for opening and closing of the valves may be automatically performed using timers. As a result, a purge gas is introduced through a pipe 8 into the treatment chamber 1. As the purge gas, air may be used, though the use of sterilized air or nitrogen gas is preferred. The purge gas is passed through the treatment chamber 1 and withdrawn therefrom through the line 11 and is then introduced through the blower 3 and the gas distributor 4 into the ISOTC adsorbing device 5. The gas from which ISOTC has been removed is withdrawn as an exhaust gas through a pipe 30 and discharged into the air. When the concentration of ISOTC vapors in the exhaust gas is decreased to a predetermined value, the blower is stopped and the door 10 is opened to take the treated article out of the chamber. Thus, the germ-destroying treatment process is over. By repeating the above operations, the germ-destroying treatment may be further continued.

While a treatment device of a batch system is shown in FIG. 2, a treatment device of a continuous system may be adopted by using a structure capable of continuously feeding and discharging articles. The basic operation in this case is similar to that described above. However, it is necessary to continuously feed a gas containing a determined concentration of ISOTC vapors to a germ destroying treatment chamber. For this purpose, a pipe 20 having an open-close valve 21 capable of controlling a flow rate of a gas may be provided between the gas distributor 4 and the treatment chamber 1 as shown in FIG. 2, so as to introduce a portion of air introduced into the gas distributor 4 into the treatment chamber 1 through the pipe 20 while controlling the proportion of the gas flow rates flowing through the pipes 20 and 18.

According to the above-described germ-destroying treatment, various articles such as foods may be efficiently sterilized in a safe manner. In this case, the ISOTC vapor-containing gas in the treatment chamber is fed, after completion of the treatment, to the ISOTC-adsorbing device together with a purge gas, where ISOTC is removed by adsorption. Thereafter the gas is discharged to the air. As a consequence, the strong irritating odor of ISOTC does not emanate during the process, so that deterioration of working environment may be prevented.

In FIG. 3, indicated as 1 is an ISOTC vapor-generating device, as 2 a closed space, as 3 an ISOTC vapor-adsorbing device and as 4 and 5 are blowers.

The ISOTC vapor-generating device 1 is provided with heating and cooling mechanisms and is constructed to accommodate ISOTC therewithin. The ISOTC Present in the device 1 may be in the form of a liquid, a solution or a gel. It may also be present in a form supported by impregnation in a porous substance.

The ISOTC vapor-adsorbing device 3 contains an adsorbent therewithin and is adapted to remove ISOTC vapors contained in a feed gas by adsorption. Any adsorbent may be used as long as it can adsorb ISOTC vapors,.

In treating the closed space 2 for germ-destroying purposes, the blower 4 is actuated to cause air to pass through the ISOTC vapor-generating chamber 1 through a line 6 and to let the ISOTC vapor-containing gas introduced into the space 2 through a line 8. When the concentration of ISOTC vapors in the space 2 is increased to a predetermined value, a valve 7 is closed while recirculating the gas within the space using a valve 10, thereby to effect the germ-destroying treatment of the closed space.

After completion of the treatment, the blower is stopped and the valve 10 is closed. Valves 15 and 12 are opened and a blower 13 is actuated. By this, a purge gas is fed through a line 14 to the closed space 2 so that an ISOTC vapor-containing gas is discharged therefrom and is introduced into the ISOTC vapor-adsorbing device 3 where the ISOTC vapors contained therein are removed by adsorption. The resulting ISOTC vapor-free gas is discharged through a line 16. In like manner, the closed space is sterilized and the ISOTC vapors used in the sterilization treatment is removed from the space. Therefore, the space is free of irritating odor attributed to ISOTC vapors.

Though air may be used as the above purge gas, the use of sterilized air or nitrogen gas is preferred.

In the present invention, it is preferable to install at least a portion of the ISOTC vapor-generating chamber 1, the blowers 4 and 5 and the ISOTC vapor-adsorbing device in the closed space according to the size of the space. When the closed space is small, they are installed outside thereof.

The concentration of the ISOTC vapors in the closed space is 5–2,000 ppm, preferably 10–500 ppm, and the ISOTC vapors are retained in the closed space for 1 minute to 12 hours. By the use of these conditions, harmful microorganisms in the closed space may be almost completley destroyed.

According to the above-described method, the air within the closed space and surfaces of machines and equipments disposed therein may be effectively sterilized. Further, since ISOTC does not corrode metals, there is no fear of corrosion of metals. Moreover, even when ISOTC vapors remain unremoved in trace amounts, they do not adversely affect human bodies.

The present invention will next be described by way of examples but is not limited thereto. In the following, parts and % are by weight unless otherwise specifically noted.

EXAMPLE 1

Allyl isothiocyanate was dissolved in an edible oil (soybean oil) as an oily liquid to obtain an ISOTC solution.

This solution was tested by sense for change in degree of emanation of allyl isothiocyanate with time. In this test, 5 g of the ISOTC solution were placed in a "schale" (dimension; diameter: 75 mm, height: 20 mm) and strength of odor emanating from the "schale" at room temperature was judged based on the following ratings. The results are shown in Table 1.

A: Eyes smart from irritating odor
B: Smell of mustard
C: Slight smell of mustard
D: No smell For the purpose of comparison, 0.05 g of allyl isothiocyanate were placed in a "schale" of the same size as above and similar test was performed. The irritating odor causing eyes to smart emanated for 30 minutes but, after 1 hour, no odor was detected.

TABLE 1

| Concentration of allyl isothiocyanate in solution (%) | Time passed (day) 30 min. | 1 | 5 | 10 | 15 | 20 |
|---|---|---|---|---|---|---|
| 0.5 | B | C | C | C | C | D |
| 1 | B | B | C | C | C | C |
| 5 | A | A | B | B | B | C |
| 10 | A | A | B | B | B | B |
| 20 | A | A | A | B | B | B |
| 30 | A | A | A | A | B | B |

EXAMPLE 2

Allyl isothiocyanate was dissolved in corn oil to obtain ISOTC solutions with various concentrations. Each solution (about 9 g) was placed in a "schale" having a diameter of 85 mm (bottom area: 56.7 $cm^2$) and a height of 15 mm. The "schale" was placed in a closed, constant-temperature vessel (volume: 88 liters) and the change of the amount of evaporation of allyl isothiocyanate was investigated. The results are shown in Table 2. The amount of evaporation of allyl isothiocyanate shown in Table 2 is in terms of parts by weight of allyl isothiocyanate evaporated per 100 parts by weight of the solution present in the "schale" at the start of the measurement.

TABLE 2

| Concentration of ISOTC | Amount of evaporation (part by weight) Time passed (hr) 1 | 2 | 3 | 4 | 5 | 6 |
|---|---|---|---|---|---|---|
| 100 | 13.3 | 22.9 | 33.7 | 47.0 | 56.2 | 66.2 |
| 50 | 9.0 | 18.5 | 27.0 | 33.9 | 37.1 | 39.9 |
| 23 | 7.8 | 15.2 | 20.7 | 24.9 | 27.2 | 29.8 |
| 20 | 5.9 | 10.5 | 14.6 | 17.5 | 19.3 | 19.7 |
| 5 | 1.3 | 2.2 | 2.9 | 3.4 | 3.9 | 4.2 |
| 0.5 | 0.14 | 0.2 | 0.26 | 0.3 | 0.33 | 0.36 |

EXAMPLE 3

Allyl isothiocyanate was dissolved in corn oil to obtain a 50% ISOTC solution. Granules (diameter: about 1 mm, length: about 3.5 mm) of calcined diatomaceous earth (100 parts) was impregnated with this solution (40 parts) to obtain an ISOTC vapor-generating agent. The change of the amount of evaporation of ISOTC with time was investigated in the same manner as that in Example 2. The results are shown in Table 3. The amount of evaporation of allyl isothiocyanate shown in Table 3 is in terms parts by weight of allyl isothiocyanate evaporated per 100 parts by weight of the solution present in the "schale" at the start of the measurement.

TABLE 3

| Time passed | 1 | 2 | 3 | 4 | 5 | 6 |
|---|---|---|---|---|---|---|
| Evaporation amount | 4.4 | 10.1 | 12.9 | 14.3 | 14.6 | 14.9 |

TABLE 3-continued

| Time passed (parts by weight) | 1 | 2 | 3 | 4 | 5 | 6 |
|---|---|---|---|---|---|---|

EXAMPLE 4

Allyl isothiocyanate was dissolved in corn oil to obtain solutions with concentrations of 50 (v/v) %, 20 (v/v) %, 10 (v/v) % and 5 (v/v) %. Mildew germs to be tested were exposed in a closed space (room temperature) to vapors emanating from the solutions. Thereafter, they were incubated at 28° C. for 3 days to investigate growth of germs. The results were as shown in Table 4.

The mold germs subjected to the test are three kinds of eumycetes specified in JIS Z 2911-1981 (Anti-mold Test Method); Penicillium Funiculosum Thom IFO 6345, green mold, referred to as Germ A in Table 4), Chaetomiun globosum Kunze ex Fries IFO 6347 (belonging to Chaetomium, referred to as Germ B in Table 4), and Cladosporium cladosporiolides (Fresenius) de vries IFO 6348 (FERM S-8; IAM F517, belonging to Kurokawa mold, referred to as Germ C in Table 4).

The above three mold germs were found to completely destroyed upon 15 minutes exposure to vapors from the 50 (v/v) % ISOTC solution and upon 120 minutes exposure to vapors from the 5 (v/v) % ISOTC solution.

TABLE 4

| Germ | Concentration of ISOTC in solution (%) | Number of cells remaining after germ-destroying treatment (%) Exposure time (minutes) | | | | | | | |
|---|---|---|---|---|---|---|---|---|---|
| | | 0 | 2 | 4 | 8 | 15 | 30 | 60 | 120 |
| A | 50 | 100 | 0 | | | | | | |
| | 20 | 100 | 87.2 | 62.4 | 0 | | | | |
| | 10 | 100 | 85.4 | 66.7 | 30.2 | 0 | | | |
| | 5 | 100 | 86.4 | 71.8 | 19.4 | 5.8 | 0 | | |
| B | 50 | 100 | 42.6 | 0 | | | | | |
| | 20 | 100 | 85.7 | 30.4 | 24.5 | 1.0 | 0 | | |
| | 10 | 100 | 60.6 | 32.3 | 18.2 | 5.1 | 0 | | |
| | 5 | 100 | 62.7 | 36.6 | 16.9 | 10.2 | 0 | | |
| C | 50 | 100 | 33.3 | 24.2 | 19.7 | 0 | | | |
| | 20 | 100 | 95.9 | 64.9 | 35.1 | 18.9 | 0 | | |
| | 10 | 100 | 71.7 | 64.6 | 46.0 | 28.3 | 15.0 | 0 | |
| | 5 | 100 | 74.8 | 57.0 | 53.3 | 37.4 | 17.8 | 9.3 | 0 |

EXAMPLE 5

In one vessel (about 3 liters) was placed a dried fish (horse mackerel) while in another vessel was placed 10 cc of 1% allyl isothiocyanate solution in soybean oil in an open state in addition to a dried fish (horse mackerel). The vessels were lid and allowed to stand at room temperature. The dried fish in each vessel was occasionally taken out therefrom for examine the odor. As a result, the dried fish stored together with the allyl isothiocyanate solution was found to retain its fish-like smell inherent to dried fish even after 6 days. In contrast, the dried fish stored by itself was found to generate a putrid smell and to be poor in freshness.

EXAMPLE 6

Example 5 was repeated in the same manner as described except that cut rice-cake was used in place of the dried fish. As a result, mold was found to form after 3 days on the rice-cake stored by itself, whereas no mold was found to form even after 1 month in the case of the rice-cake stored together with the allyl isothiocyanate solution.

EXAMPLE 7

Mustard seeds (30 parts by weight) were mixed with an edible oil (soybean oil, 70 parts by weight). The mixing was able to easily performed without causing deterioration of the working environment since mustard seeds were almost free of irritating odor of an isothiocyanate.

This ISOTC solution was tested by sense for change in degree of emanation of allyl isothiocyanate with time. In this test, 20 g of the ISOTC solution were placed in a "schale" (dimension; diameter: 70 mm, height: 15 mm) and strength of odor emanating from the "schale" at room temperature was judged based on the following ratings. The results are shown in Table 5.

A: Eyes smart from irritating odor
B: Smell of mustard
C: Slight smell of mustard
D: No smell

TABLE 5

| Time passed | 30 minutes | 1 day | 5 days | 10 days | 15 days | 20 days |
|---|---|---|---|---|---|---|
| Strength of Odor | D | C | C | C | C | C |

For the purpose of comparison, 0.05 g of ally isothiocyante were placed in a "schale" of the same size as above and similar test was performed. The irritating odor causing eyes to smart emanated for 30 minutes but, after 1 hour, no odor was detected.

EXAMPLE 8

Allyl isothiocyanate was dissolved in a commercially available edible oil (soybean oil) to obtain solutions with concentrations of 1-10%. 10 parts of each ISOTC solution were homogeneously mixed and dispersed into 100 parts of carrageenan gel obtained from 5% of carrageenan and 95% of water, thereby to obtain a gel like material containing allyl isothiocyanate.

Each of the gel-like materials was then tested by sense for change in degree of emanation of allyl isothiocyanate with time. In this test, 5 g of the gel-like material were placed in a "schale" (dimension; diameter: 75 mm, height: 20 mm) and strength of odor emanating from the "schale" at room temperature was judged based on the following ratings. The results are shown in Table 6.

A: Eyes smart from irritating odor

B: Smell of mustard
C: Slight smell of mustard
D: No smell

For the purpose of comparison, 0.05 g of ally isothiocyanate were placed in a "schale" of the same size as above and similar test was performed. The irritating odor causing eyes to smart emanated for 30 minutes but, after 1 hour, no odor was detected.

TABLE 6

| Sample No. | Concentration of allyl isothiocyanate in solution (%) | Time passed (day) | | | | | |
|---|---|---|---|---|---|---|---|
| | | 60 min. | 2 | 3 | 5 | 10 | 14 | 20 |
| 1 | 1 | B | B | C | C | D | D | D |
| 2 | 2 | B | B | B | C | C | C | D |
| 3 | 3 | A | B | B | B | B | C | C |
| 4 | 5 | A | B | B | B | B | B | B |
| 5 | 1 | A | B | B | B | B | B | B |

EXAMPLE 9

The gel-like material (10 g) of Sample No. 4 of Example 8 was placed in a beaker and this beaker in turn was placed in a commercially available, air-tight, plastic vessel (dimension; length: 150 mm, width: 200 mm, height: 150 mm) together with a commercially available, cut rice-cake. After covering with a lid for sealing, the vessel was allowed to stand at ambient temperature.

For the purpose of comparison, similar test was repeated in the same manner as described above except that no gel-like material was used.

As a result of the above preservation test of the rice-cake, mold was found to form after three days from the commencement of the preservation in the case of the comparative test wherein no gel-like material of the present invention was used. In contrast, in the test wherein the gel-like material of the present invention was used, no mold was found to form on the surface of the rice-cake even after 30 days preservation. This suggests that the gel-like substance has excellent anti-mold property, excellent germicidal property and excellent freshness-retaining property.

EXAMPLE 10

Example 9 was repeated in the same manner as described except that bread was used in place of the rice-cake. As a result, while mold was found to form after 3 days preservation in the comparative test in which no gel-like material of the present invention was used, no mold was found to form even after 30 days preservation in the case of the test wherein the gel-like material of the present invention was employed.

EXAMPLE 11

(1) Preparation of Samples

Bread is sliced to a thickness of 1 cm and the following three groups of samples (A, B and C) were prepared:

A group: Three slices of bread were inserted into respective polyethylene bags (thickness: 100 μm) and each of the bags was then heat-sealed.

B group: Three slices of bread were inserted into respective polyethylene bags (thickness: 100 μm). Into each of the bags was further inserted a polyethylene bag (thickness: 30 μm) containing an ISOTC solution composed of 20 cc of soybean oil and 10% of allyl isothiocyanate. The resulting bags were then heat-sealed.

C group: Three slices of bread were inserted into respective polyethylene bags (thickness: 100 μm). Each of the bags was then evacuated and heat-sealed. These bags were then placed in an air-tight vessel with an inside volume of about 2 liters. This vessel contained about 5 cc of allyl isothiocyanate at 25° C. so that the inside thereof was filled with allyl isothiocyanate vapors. The bread-containing bags were retained in the vessel for 1 hour.

(2) Test Results

Three bags of each of the groups A-C (total 9 bags) were allowed to stand at room temperature to see whether or not each bread in the bag was molded. The results are shown in Table 7.

TABLE 7

| Sample | Time passed (day) | | | | | |
|---|---|---|---|---|---|---|
| | 1 | 3 | 7 | 10 | 20 | 30 |
| Group A | — | ++ | +++ | +++ | +++ | +++ |
| Group B | — | — | — | — | — | — |
| Group C | — | — | — | — | — | — |

Remarks:
—Not molded
+ 1 or 2 molds formed
++ 3 or 4 molds formed
+++ 5 or more molds formed. Or round mold spread to a diameter of at least 1 cm.

EXAMPLE 12

Allyl isothiocyanate was dissolved in 99% ethanol a proportion of 0.5% by weight to obtain a spray solution. This solution (300 g) was charged in an aerosol can with an inside volume of 500 ml together with 80 g of a jetting agent (liquefied butane) to obtain a jetting device. When jetted from the jetting device, the solution was found to be sprayed to form uniform fog-like particles. It was confirmed that, in this spraying operation, strongly irritating odor of allyl isothiocyanate was significantly prevented and the environment was not adversely affected.

Using this jetting device, the solution was sprayed into an air-tight vessel containing a cut rice-cake. After closing with a lid, the vessel was allowed to stand for 1 month. No mold was found to form. For the purpose of comparison, a test was performed without spraying the solution. The surface of the rice-cake was molded after three days.

EXAMPLE 13

100 Parts by weight of a 1% by weight solution of allyl isothiocyanate in ethanol were mixed with 100 parts by weight of soybean oil to obtain a spray solution. This solution was charged in an aerosol can in the same manner as Example 12 together with a jetting agent to obtain a jetting device. When jetted from the jetting device, the solution was found to be sprayed to form uniform fog-like particles. It was confirmed that, in this spraying operation, irritating odor of allyl isothiocyanate was much more prevented in comparison with Example 12.

EXAMPLE 14

A commercially available, small, batch-wise vacuum drying device having a drying chamber therein and provided with an evacuation port, an air feed port and an air-tight door in the wall thereof was provided. To the evacuation port was connected a vacuum pump via adsorbing agent packed with activated carbon. Further, a gas discharge pipe of an ISOTC reservoir was connected via three-way open-close valve to the air feed port. The reservoir was packed with sepiolite powder impregnated with allyl isothiocyanate ISOTC vapor-generating agent) and has a wall portion where the discharge pipe was provided. A germ-destroying device according to the present invention was thus constructed.

The door of this device was opened and a cut rice-cake seal-packed in a polyethylene bag was placed in the device. After closing the door, the three-way valve was turned to an open position to introduce ISOTC vapors from the ISOTC reservoir into the drying chamber of the device. This condition was kept for 24 hours. Thereafter, the vacuum pump was actuated and the three-way valve was turned to shut the ISOTC reservoir side and to open the air inlet side, thereby withdrawing the ambient gas within the drying chamber while removing the ISOTC vapor contained therein in the adsorption tower.

After stopping the operation of the vacuum pump, the door of the drying chamber was opened to take the packed rice-cake out thereof. The packed rice-cake as such was then allowed to stand in the air.

For the purpose of comparison, a rice-cake was seal-packed in a polyethylene in a similar manner and was allowed to stand in the air without subjecting to a germ-destroying treatment.

The rice-cake was molded after standing for 3 days in the case of the comparison test. In contrast, the rice-cake which had been subjected to the germ-destroying treatment according to the present invention was not molded even after standing for 1 month.

We claim:

1. A method for the treatment of an article for destroying germs comprising:

packaging said article in a packing material permeable to vapors of an isothiocyanate to form a package; and contacting the exterior of the package with a gas containing vapors of the isothiocyanate to allow the vapors to permeate through the packing material into the package to destroy germs within the package and then to permeate back through the packing material out of the package.

2. A method for the treatment of an article for destroying germs comprising:

introducing an isothiocyanate in the form of vapors or liquid microparticles into a treatment chamber to form an isothiocyanate vapor-containing atmosphere in said treatment chamber;

packaging said article with a packing material permeable to vapors of the isothiocyanate to form a package;

feeding the package into the treatment chamber;

contacting the exterior of the package with said isothiocyanate vapor-containing atmosphere in the treatment chamber to allow said vapors to permeate through said packing material into the package to destroy germs in said article and then to permeate back through said packing material out of the package;

discharging said isothiocyanate vapor-containing atmosphere from said germ-treatment chamber after said contacting; and separating the isothiocyanate vapors from the discharged gas.

* * * * *

UNITED STATES PATENT AND TRADEMARK OFFICE
CERTIFICATE OF CORRECTION

PATENT NO. : 5,246,663
DATED : September 21, 1993
INVENTOR(S) : OHAMA et al

It is certified that error appears in the above-indentified patent and that said Letters Patent is hereby corrected as shown below:

On the Title Page, please add the following:

[30]     Foreign Application Priority Data

```
     Apr.  7, 1989 [JP]    Japan............... 1-88274
     Apr.  7, 1989 [JP]    Japan............... 1-88275
     Apr.  7, 1989 [JP]    Japan............... 1-88276
     Apr.  7, 1989 [JP]    Japan............... 1-88277
     Apr. 14, 1989 [JP]    Japan............... 1-94770
     May  30, 1989 [JP]    Japan............... 1-137792
     May  30, 1989 [JP]    Japan............... 1-137793
     Sep. 14, 1989 [JP]    Japan............... 1-239554
     Sep. 14, 1989 [JP]    Japan............... 1-239555 --
```

Signed and Sealed this

Thirteenth Day of September, 1994

Attest:

BRUCE LEHMAN

Attesting Officer    Commissioner of Patents and Trademarks